United States Patent [19]

Liu et al.

[11] Patent Number: 5,493,018

[45] Date of Patent: Feb. 20, 1996

[54] PROCESS FOR SYNTHESIZING CARBAPENEM INTERMEDIATES USING A RHODIUM CATALYST AND LEWIS ACID

[75] Inventors: Thomas Meng-Han Liu, Westfield; Joseph E. Lynch, Plainfield; Ralph P. Volante, Cranbury, all of N.J.

[73] Assignee: Merck & Co., Inc., Rahway, N.J.

[21] Appl. No.: 186,207

[22] Filed: Jan. 25, 1994

[51] Int. Cl.$^6$ .......................... C07D 487/04; A61K 31/40
[52] U.S. Cl. ............................................. 540/302; 540/350
[58] Field of Search ...................................... 540/302, 350

[56] References Cited

U.S. PATENT DOCUMENTS

| | | | |
|---|---|---|---|
| 4,287,123 | 9/1981 | Liu et al. | 260/239 A |
| 4,349,687 | 9/1982 | Liu et al. | 549/291 |
| 4,378,315 | 3/1983 | Christensen et al. | 260/239 A |
| 4,467,107 | 8/1984 | Liu et al. | 560/170 |
| 4,473,502 | 9/1984 | Liu et al. | 260/239 A |
| 4,499,278 | 2/1985 | Melillo et al. | 548/240 |
| 4,739,048 | 4/1988 | Christensen et al. | 540/350 |
| 4,816,577 | 3/1989 | Bender et al. | 540/200 |
| 4,866,171 | 9/1989 | Kumagai et al. | 540/350 |

OTHER PUBLICATIONS

Reider, Paul J. et al. Tet. Let. 23 (22):2293–2296 (1982).
Salzmann, Thomas N. et al. J. Am. Chem. Soc. 102:6161–6163 (1980).
Melillo, D. G., et al. Tet. Let. 21:2783–2786 (1980).
Fuentes, L. M. et al. J. Am. Chem. Soc. 108:4675–4676 (1986).
de Vries, J. G. et al. Heterocycles 23 (8):1915–1919 (1985).
Ihara, M. et al. J. Chem. Soc. Perkin Trans I 2215–2221 (1989).
Karady, S. et al. J. Am. Chem. Soc. 103:6765–6767 (1981).

*Primary Examiner*—Rebecca Cook
*Attorney, Agent, or Firm*—Richard C. Billups; Mark R. Daniel

[57] ABSTRACT

This invention relates to the synthesis of a bicyclic ketoester compound of the formula 1 obtained by cyclizing a diazo compound of formula 2: in the presence of a rhodium catalyst.

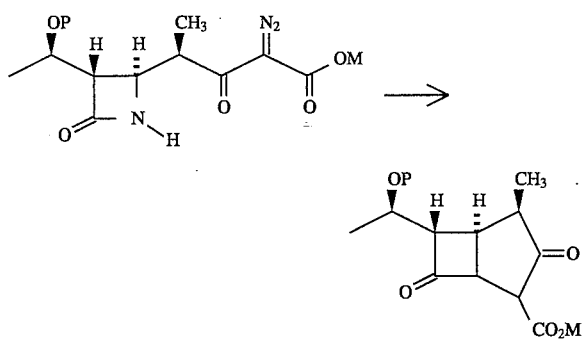

By adding an effective amount of a Lewis acid to the cyclization reaction, the reaction selectively produces the 1-beta methyl isomer, and epimerization of the 1-beta methyl compound to the 1-alpha isomer is minimized.

17 Claims, No Drawings

PROCESS FOR SYNTHESIZING CARBAPENEM INTERMEDIATES USING A RHODIUM CATALYST AND LEWIS ACID

BACKGROUND OF THE INVENTION

The present invention relates to the synthesis of a beta methyl carbapenem intermediate of the formula:

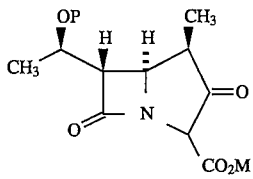

This intermediate for carbapenem antibiotics has been disclosed in numerous patents and publications. For example, the intermediate is disclosed in U.S. Pat. No. 4,350,631 issued to Christensen, et al. on Sep. 21, 1982 and in U.S. Pat. No. 4,994,568 issued to Christensen on Feb. 19, 1991. In the process described in each of these patents, a diazo compound of the formula:

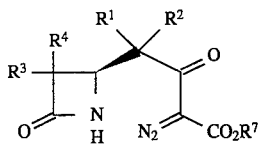

is cyclized using a catalyst or irradiation. These process steps generate a mixture of 1-α and 1-β methyl isomers, which in turn require separation prior to further chemical modification.

Likewise, a washing step has been utilized in the past, whereby the diazo compound is purified in an aqueous medium. The diazo compound is washed with water, dried and then cyclized. This improves the yield of the 1-β methyl isomer, but introduces water into the reaction, thus necessitating the implementation of the drying step. Drying at this stage in the synthesis of carbapenems can be unpredictable and dangerous.

The present invention overcomes these difficulties, providing an unexpectedly low rate of formation of the 1-α methyl isomer, and thus eliminating the need for separation of the α and β isomers prior to further chemical synthesis. Moreover, even in relatively uncontrolled reactions, inclusion of the Lewis acid as described herein in detail can reduce epimerization to the 1-α methyl compound to less than about one percent.

SUMMARY OF THE INVENTION

A process for synthesizing a 1-β methyl compound of the formula:

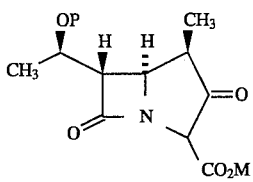

is disclosed, in which M represents a carboxyl protecting group and P represents H or a hydroxyl protecting group, wherein the compound:

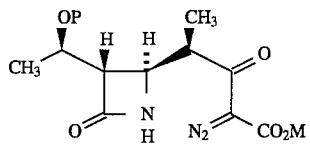

is cyclized in the presence of a rhodium catalyst and a catalytic quantity of a Lewis acid which is effective for reducing the formation of the 1-α methyl isomer.

DETAILED DESCRIPTION OF THE INVENTION

The 1-β methyl isomer of the bicyclic ketoester 1 which is shown above is highly desired and useful as a carbapenem intermediate, due to the recognition in the art that 1-beta methyl final carbapenem compounds have a reduced tendency toward biological inactivation by the enzyme dehydropeptidase, when administered to treat bacterial infections. Generally, the 1-β methyl isomer of the final product is more resistant to deactivation than the 1H or the 1-α methyl isomer.

The 1-β methyl isomer of the bicyclic ketoester can further be reacted at the 2-position to establish a leaving group at this position, which can further be reacted as described in numerous patents and published applications to form the appropriate carbapenem end product with a substituent group at position two.

The present invention is thus an improvement in the process of synthesizing the 1-β methyl bicyclic ketoester 1. The improvement in the process is comprised of the addition of a Lewis acid to the reaction mixture which effectively prevents the formation of the 1-α methyl isomer and further essentially prevents epimerization of the 1-β methyl isomer.

As used herein, the term "rhodium catalyst" refers to dimeric rhodium salts selected from the group consisting of rhodium octanoate $Rh_2(Oct)_4$, rhodium acetate $Rh_2(Ac)_4$, rhodium acetamide $Rh_2(HNAc)_4$ and rhodium trifluoroacetate $Rh_2(O_2CCF_3)_4$.

Illustrated below as a catalyst for use in the process described herein is $Rh_2(Oct)_4$, present in a catalytic amount which is effective for converting the diazo compound 2 to the bicyclic ketoester 1.

The term "Lewis Acid" is used herein to refer to those Lewis acids which are effective in forming the 1-beta methyl isomer upon cyclization, and for substantially preventing isomerization of the 1-beta methyl isomer to the less desirable 1-alpha methyl isomer. Examples of suitable Lewis acids include but are not limited to the following: $MgCl_2$, $MgBr_2$, $Mg(OAc)_2$, $Mg(O_3SCF_3)_2$, $ZnCl_2$, $ZnBr_2$, $Zn(OAc)_2$, $Zn(O_3SCF_3)_2$, $SnCl_2$, $SnBr_2$, $Sn(O_3SCF_3)_2$, $SnCl_4$, $SnBr_4$, $TiCl_4$, $Ti(OiPr)_4$, $TiCl_n(OiPr)_{4-n}$, with n=0, 1, 2, 3 or 4, $CaCl_2$, $CaSO_4$, $GaCl_3$, $FeCl_2$, $FeCl_3$, $CuCl$, $CuBr$, $CuCl_2$, $CuBr_2$, $PdCl_2$, $Pd(OAc)_2$, $BF_3 \cdot OEt_2$, $BCl_3$, $R_2B(O_3SCF_3)$, with R=$C_{1-4}$ alkyl), $BBr_3$, $B(OPh)_3$, $B(OCH_3)_3$, $AlCl_3$, $LiCl$ and $LiClO_4$.

As used above, the abbreviation Ac means acetate ($CH_3C(O)$—); Et means ethyl, Ph means phenyl and OiPr means isopropoxide (—$OCH(CH_3)_2$). With respect to the titanium catalyst noted above, $Ti(OiPr)_4$ refers to titanium isopropoxide $Ti(OCH(CH_3)_2)_4$.

The term $C_{1-4}$ alkyl means —$CH_3$, —$CH_2CH_3$, —$CH_2CH_2CH_3$, —$CH_2CH_2CH_2CH_3$, —$CH(CH_3)_2$, —$CH_2CH(CH_3)_2$, —$CH(CH_3)CH_2CH_3$ and —$C(CH_3)_3$.

A subset of the Lewis acids for use in the process described herein is comprised of $ZnBr_2$ and $MgCl_2$.

Illustrated below is the Lewis acid $ZnBr_2$ used in the process described herein.

The Lewis acid is typically used in a catalytic amount, which is an amount that is effective for forming the 1-β methyl isomer, and for preventing the epimerization of the 1-β methyl isomer to the 1-α methyl isomer. This amount typically ranges from about 0.1 to about 10 mole %, with the preferred concentration being around 1 mole %.

In the process described above, the hydroxyl group of the hydroxyethyl side chain can be unprotected or in protected form. Hence, P represents hydrogen or a hydroxyl protecting group. Examples of suitable hydroxyl protecting groups P are: t-butylmethoxyphenylsilyl, t-butyldimethylsilyl (TBDMS), t-butoxydiphenylsilyl, trimethylsilyl (TMS), triethylsilyl (TES), o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

A subset of the hydroxyl protecting groups used in the present invention is comprised of TES, TMS and TBDMS.

Likewise, in the process, the carboxyl group is typically in protected form. Examples of suitable carboxyl protecting groups M are: benzhydryl, o-nitrobenzyl, p-nitrobenzyl (PNB), 2-naphthylmethyl, allyl, 2-chloroallyl, benzyl, 2,2,2-trichloroethyl, trimethylsilyl, t-butyldimethylsilyl (TBDMS), t-butyldiphenylsilyl, 2-(trimethylsilyl)ethyl, phenacyl, p-methoxybenzyl, acetonyl, p-methoxyphenyl, 4-pyridylmethyl and t-butyl.

A subset of the carboxyl protecting groups is comprised of TBDMS and PNB. The carboxyl protecting group PNB is illustrated below.

Many other suitable hydroxyl and carboxyl protecting groups are known in the art. See, e.g., T. W. Greene, *Protective Groups in Organic Synthesis*, John Wiley & Sons, Inc., 1981 (Chapters 2 and 5).

The invention is further described in connection with the following non-limiting examples.

EXAMPLE 1

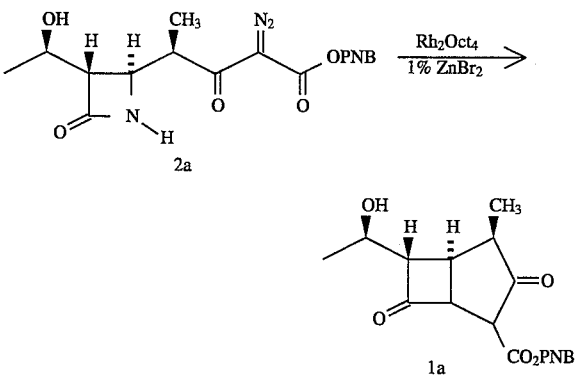

Compound 2a (43.2g, 0.111 mol) is slurried in MeOAc (987 mL). A solution of $ZnBr_2$ (246.8 mg) in THF (24.68 mL) is added, followed by a solution of $Rh_2Oct_4$ (259 mg) in MeOAc (130 mL). The mixture is heated at reflux for 90 minutes, followed by liquid chromatography with 40:60 $CH_3CN:H_2O$(0.1% $H_3PO_4$), 1.5 mL/min, YMC-AQ C-18, 260 nm, Retention Time (RT) 2a=7.6 min., RT of 1a= 3.2 min., RT of the 1-α methyl isomer=3.3 min.

Liquid Chromatography assay showed 87.5% yield of 1-β-methyl compound 1a, and no detectable 1-α methyl isomer.

EXAMPLE 2

Using the procedure set forth in Example 1, the Lewis acid $ZnBr_2$ is replaced with $MgCl_2$.

EXAMPLE 3

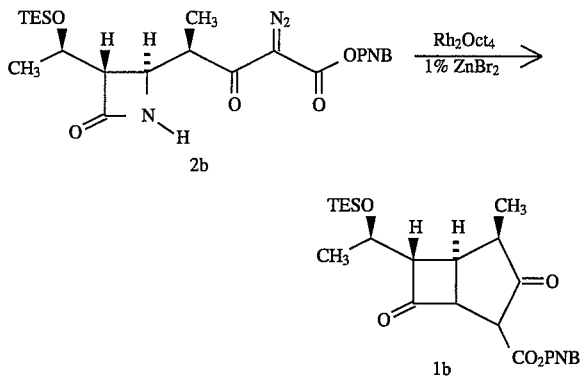

The procedure set forth in Example 1 is repeated, except that the triethylsilyl (TES) substituted compound 2b is reacted in place of compound 2a, producing compound 1b.

EXAMPLE 4

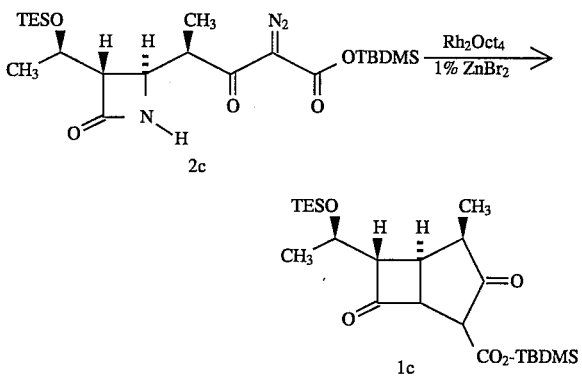

The procedure set forth in Example 1 is repeated, except that the TBDMS-substituted compound 2c is reacted in place of compound 2, producing compound 1c.

EXAMPLE 5

For purposes of comparison, Rhodium octanoate (1.05 mg) in methyl acetate (0.525 mL) was added to compound 2a (175 mg) in methyl acetate (4 mL). The solution was refluxed for 2.0h. LC analysis showed the presence of 1a and the 1-α-methyl compound in a molar ratio of 4:88.

Using the same lots of materials as above, rhodium octanoate (1.05 mg) in methyl acetate (0.525 mL) and $MgCl_2$ (0.42 mg) in THF (0.1 mL) were added to compound 2a (175 mg) in methyl acetate (4 mL). The solution was refluxed for 2.0h. LC analysis showed the presence of 1a and the 1-α-methyl compound in a molar ratio of 93:1.

What is claimed is:

1. A process for synthesizing a compound of the formula:

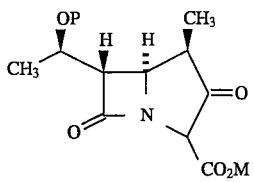

in which M is a carboxyl protecting group and P represents H or a hydroxyl protecting group, comprising cyclizing the compound:

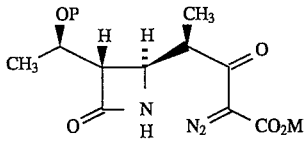

in the presence of a rhodium catalyst and a catalytic quantity of a Lewis acid which is effective for reducing formation of the 1-αmethyl isomer to form compound 1.

2. A process in accordance with claim 1 wherein the rhodium catalyst is selected from the group consisting of rhodium octanoate, rhodium acetate, rhodium acetamide and rhodium trifluoroacetate.

3. A process in accordance with claim 2 wherein the rhodium catalyst is rhodium octanoate.

4. A process in accordance with claim 2 wherein the Lewis acid is selected from the group consisting of $MgCl_2$, $MgBr_2$, $Mg(OC(O)CH_3)_2$, $Mg(O_3SCF_3)_2$, $ZnCl_2$, $ZnBr_2$, $Zn(OC(O)CH_3)_2$, $Zn(O_3SCF_3)_2$, $SnCl_2$, $SnBr_2$, $Sn(O_3SCF_3)_2$, $SnCl_4$, $SnBr_4$, $TiCl_4$, $Ti((OCH(CH_3)_2)_4$; $TiCl_n((OCH(CH_3)_2)_{4-n}$ with n=0, 1, 2, 3 or 4, $CaCl_2$, $CaSO_4$, $GaCl_3$, $FeCl_2$, $FeCl_3$, $CuCl$, $CuBr$, $CuCl_2$, $CuBr_2$, $PdCl_2$, $Pd(OC(O)CH_3)_2$, $BF_3 \cdot OEt_2$, $BCl_3$, $R_2B(O_3SCF_3)$, with $R=C_{1-4}$ alkyl, $BBr_3$, $B(OPh)_3$, $B(OCH_3)_3$, $AlCl_3$, $LiCl$ and $LiClO_4$.

5. A process in accordance with claim 4 wherein the Lewis acid is selected from the group consisting of $ZnBr_2$ and $MgCl_2$.

6. A process in accordance with claim 3 wherein the Lewis acid is selected from the group consisting of $MgCl_2$, $MgBr_2$, $Mg(OC(O)CH_3)_2$, $Mg(O_3SCF_3)_2$, $ZnCl_2$, $ZnBr_2$, $Zn(OC(O)CH_3)_2$, $Zn(O_3SCF_3)_2$, $SnCl_2$, $SnBr_2$, $Sn(O_3SCF_3)_2$, $SnCl_4$, $SnBr_4$, $TiCl_4$, $Ti((OCH(CH_3)_2)_4$; $TiCl_n((OCH(CH_3)_2)_{4-n}$ with n=0, 1, 2, 3 or 4, $CaCl_2$, $CaSO_4$, $GaCl_3$, $FeCl_2$, $FeCl_3$, $CuCl$, $CuBr$, $CuCl_2$, $CuBr_2$, $PdCl_2$, $Pd(OC(O)CH_3)_2$, $BF_3 \cdot OEt_2$, $BCl_3$, $R_2B(O_3SCF_3)$, with $R=C_{1-4}$ alkyl, $BBr_3$, $B(OPh)_3$, $B(OCH_3)_3$, $AlCl_3$, $LiCl$ and $LiClO_4$.

7. A process in accordance with claim 6 wherein the Lewis acid is selected from the group consisting of $ZnBr_2$ and $MgCl_2$.

8. A process in accordance with claim 7 wherein the Lewis acid is present in an amount ranging from about 0.1 to about 10 mole %.

9. A process in accordance with claim 8 wherein the Lewis acid is present at about 1 mole %.

10. A process in accordance with claim 1 wherein M represents a carboxyl protecting group selected from the group consisting of benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl.

11. A process in accordance with claim 10 wherein M represents t-butyldimethylsilyl or p-nitrobenzyl.

12. A process in accordance with claim 11 wherein M represents p-nitrobenzyl.

13. A process in accordance with claim 1 wherein P represents H or a protecting group selected from the group consisting of t-butylmethoxyphenylsilyl, t-butyldimethylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

14. A process in accordance with claim 13 wherein P represents triethylsilyl, trimethylsilyl or t-butyldimethylsilyl.

15. A process in accordance with claim 14 wherein P represents t-butyldimethylsilyl.

16. A process in accordance with claim 4 wherein M represents a carboxyl protecting group selected from the group consisting of benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl; and P represents H or a protecting group selected from the group consisting of t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxy-carbonyl.

17. A process in accordance with claim 7 wherein

M represents a-carboxyl protecting group selected from the group consisting of t-butyldimethylsilyl and p-nitrobenzyl, and P represents a protecting group selected from the group consisting of triethylsilyl, trimethylsilyl and t-butyldimethylsilyl.

* * * * *